United States Patent [19]
Van Wyk et al.

[11] Patent Number: 5,693,063
[45] Date of Patent: Dec. 2, 1997

[54] PROCESS FOR SHAPING AND SHARPENING A ROTATABLE SURGICAL SHAVER BLADE

[75] Inventors: Robert A. Van Wyk, Largo; Gary R. Heisler, Holiday, both of Fla.

[73] Assignee: Bristol-Myers Squibb Company, New York, N.Y.

[21] Appl. No.: 791,233

[22] Filed: Jan. 30, 1997

Related U.S. Application Data

[63] Continuation-in-part of Ser. No. 636,990, Apr. 10, 1996.
[51] Int. Cl.$^6$ ................................................. A61B 17/32
[52] U.S. Cl. ........................... 606/167; 606/170; 128/898
[58] Field of Search ................................... 606/167, 170, 606/180, 159; 128/898

[56] References Cited

U.S. PATENT DOCUMENTS

| | | |
|---|---|---|
| 4,603,694 | 8/1986 | Wheeler . |
| 5,601,583 | 2/1997 | Donahue et al. ............... 606/170 |
| 5,620,447 | 4/1997 | Smith et al. ............... 606/170 |

*Primary Examiner*—Michael Buiz
*Assistant Examiner*—Kevin Truong
*Attorney, Agent, or Firm*—Gene Warzecha

[57] ABSTRACT

A process for simultaneously shaping and sharpening a cutting widow at the distal end of a tubular member of a rotary blade assembly. The assembly is provided with a stationary elongated outer tube, having a cutting window at its distal tip and includes a rotatable elongated inner tube having a cutting member at its distal tip. The window in the outer tube has a curvilinear profile defined by a peripheral rim surrounded entirely by a land surface which is inclined relative to the rim. The inclination of the land produces an area which tapers from a full thickness, where the land is adjacent to the cylindrical wall of the outer tube, to a sharp edge around the periphery of the window. The curvilinear window is produced by a manufacturing process which creates the window opening with a sharpened periphery at the same time that the land surrounding the opening is inclined. A preferred embodiment utilizes electrochemical grinding of the distal ends of the tubular member by a tool having a rotatable wheel with a perimeter in the shape of a groove of predetermined arcuate profile.

17 Claims, 18 Drawing Sheets

PROCESS FOR SHAPING AND SHARPENING A ROTATABLE SURGICAL SHAVER BLADE

This is a continuation-in-part application of application Ser. No. 08/636,990, filed Apr. 10, 1996.

BACKGROUND OF THE INVENTION

1. Field of the Invention

The invention relates to elongated, powered surgical instruments for use in endoscopic tissue resection. More particularly, the invention relates to an instrument having an elongated inner tube rotatably situated within an elongated stationary outer tube, both inner and outer tubes having, at their distal ends, cutting apertures which cooperate to resect or otherwise affect tissue during endoscopic surgical procedures. Still more particularly, the invention relates to the method of manufacturing the cutting aperture at the distal end of an elongated tubular member of a rotatable surgical instrument.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member has a surface or edge for engaging tissue via the opening in the outer tubular member and in many cases (but not all) cooperates with the opening to shear, cut or trim tissue. In some cases, such as burrs, the opening in the outer tube merely allows access to the tissue and does not otherwise cooperate to resect tissue. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as shaver blades. Cut tissue is aspirated through the hollow lumen of the inner tubular member to be collected via a vacuum tube communicating with the handpiece.

The aforementioned elongated surgical cutting instruments have also been produced in angled configurations in which the distal tips of the inner and outer members are aligned and offset or bent at either a fixed or variable angle from the proximal ends of the aligned inner and outer members. Examples of fixed and variable angle rotary surgical instruments are shown in U.S. Pat. Nos. 4,646,738 (Trott) and 5,411,514 (Fucci et al.), both assigned to the assignee hereof, and incorporated by reference herein. In other respects the operation of fixed and variable angle shavers is largely the same as that of the straight shavers described above.

One parameter affecting the efficiency of operation of shaver blades is sharpness of the edges of the windows. Various prior art designs are known to have differing degrees of sharpness of both the inner cutting edges and the periphery of the outer window. The present invention is concerned with the design and manufacture of an outer tubular member having a sharpened window periphery.

It is known that improved resection efficiency is achieved by sharpening the cutting edges and this is true of conventional scissors as well as endoscopic shavers although the manufacture of the latter is considerably more difficult. The smaller the included angle of the cutting edge, the sharper the edge. Clearly, below a certain limit the edge becomes too delicate to be practical. When applied to the tubular members of cylindrical, rotating shavers, the cutting edges on the inner member and the periphery of the outer window are the cooperating edges which should have the smallest included angles in order to produce sharp edges. However, this must be balanced with cost and speed of manufacture. In prior art designs, the outer window is sometimes formed by simply grinding or milling an opening at the distal tip of the outer tube, the opening lying in a plane angled relative to the tube axis. Thus, the outer window faces toward the end of the tube as well as toward the side. It will be understood that this process produces a generally elliptical window periphery which has a lower included angle at its proximal end and a larger included angle at its distal end. A land surface surrounds the periphery and is angled (in the cutting plane) such that the inner rim of the land defines the sharpened cutting edge of the outer member. The formation of this type of outer window could be achieved by a variety of two-dimensional through-cutting processes such as wire EDM (electrical discharge machining), ram EDM, conventional or electrochemical grinding or milling. For certain purposes, this type of cutting window may be sufficient, however, it is known that subjecting the land surface to additional processing can produce a sometimes more preferable "three-dimensional" window shape and sharper edge. The term "three-dimensional" is used to distinguish the opening from one formed by a simple planar cut through the tip of a tube: the periphery of the latter lies only in a two-dimensional plane while the periphery of the former also extends above and below this plane. However, the additional steps required to produce such sharpness entail the use of either a tool having a complex contour or a machining process capable of complex contouring motions (e.g., a computer numerical control (CNC) machine). Additionally, practical manufacture of these devices would be hampered because simultaneous production of several blades is more difficult with such processes, if at all possible.

It is accordingly an object of this invention to produce an outer member of a shaver blade assembly in which the window of the outer member has a sharpened periphery.

It is also an object of this invention to produce a shaver blade assembly having an outer member with a sharpened window formed by a peripheral land surface angled to the window rim.

It is another object of this invention to produce a sharpened outer window with a simple process minimizing the use of complex tools and the number of required processing steps.

It is yet another object of this invention to shape and sharpen a three-dimensional window in a tubular member of a rotatable surgical instrument with a single step process.

SUMMARY OF THE INVENTION

These and other objects of this invention are achieved by the preferred embodiment disclosed herein which is a method of forming an opening at one end of an elongated tubular surgical shaver blade having a distal end and a proximal end. The method comprises the steps of providing an electrochemical grinding apparatus having a rotatable abrasive wheel which has a perimetral surface with a circumferential groove formed in the surface. The groove has a predetermined arcuate profile in a radial plane of the wheel. The method further comprises securing the distal end of the elongated tubular surgical shaver blade in a predetermined orientation relative to the wheel and moving the distal end of the shaver blade relative to the wheel during the performance of an electrochemical grinding process.

In another aspect the invention lies in a method comprising the steps of inclining the tubular members at a predetermined angle relative to the wheel and moving the closed, rounded ends of the tubular members tangentially over the arcuate perimetral surface of the wheel.

DESCRIPTION OF THE PREFERRED EMBODIMENT

Figure 1:
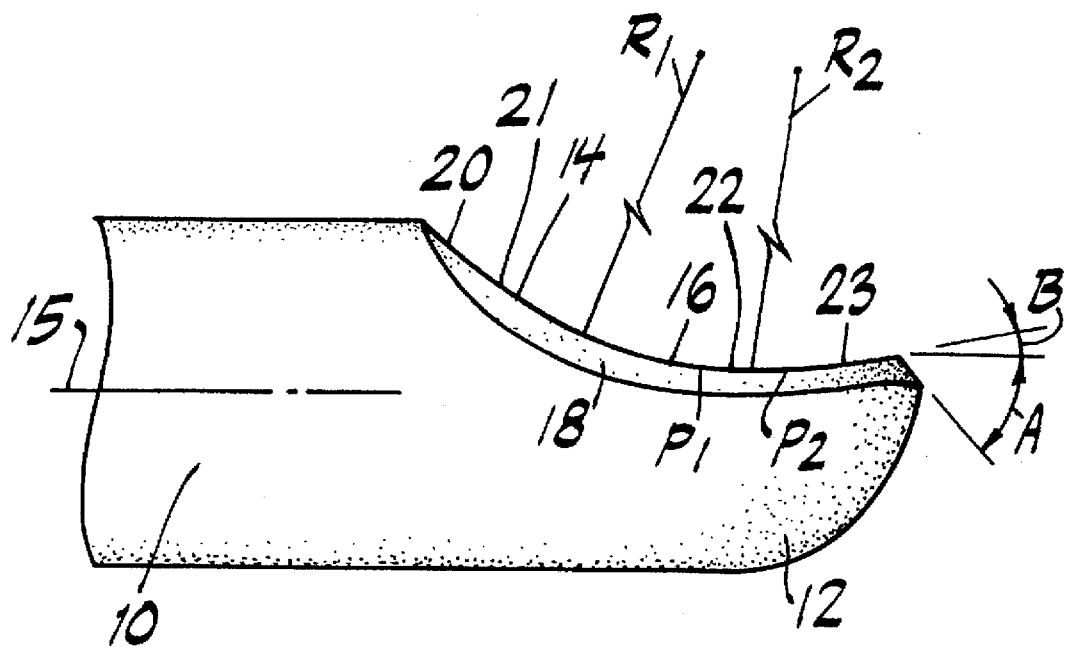
FIG. 1 is a side elevational view of the distal tip of a prior art outer tube having a curvilinear cutting window.
Figure 2:
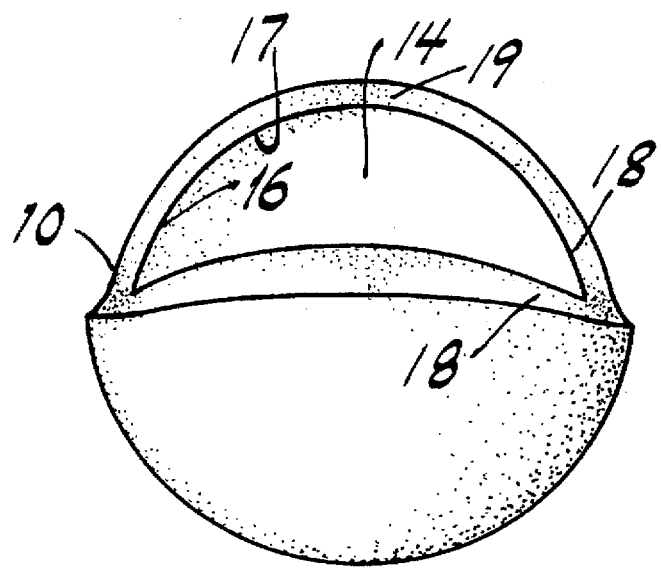
FIG. 2 is an end view of FIG. 1.
Figure 3:
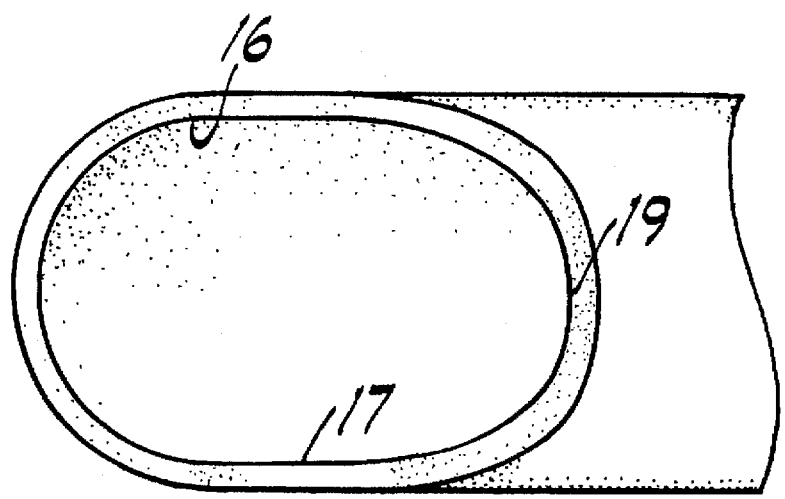
FIG. 3 is a plan view of FIG. 1.

FIGS. 1 and 2 show a distal tip of a prior art outer tubular member 10 of a rotary shaver blade assembly (not to scale). The proximal ends of the tubular member are conventional and well understood by those skilled in the art. Outer tubular member 10 has a distal tip 12 with a curvilinear cutting window 14 which faces to the side, i.e. laterally, perpendicular to axis 15, and away from the end of the blade, i.e. longitudinally in a direction parallel to axis 15. The terms "laterally" and "longitudinally" mean that the interior of the outer tubular member is visible when viewed from these vantage points. The window has a peripheral rim 16 which is formed by the intersection of the window with the interior surface 17 of the outer tube and is surrounded by a land 18 which is angled at its distal end at an angle A relative to axis 15 and the distal tip of window periphery 16. Angle A appears to be formed by a complex grinding or shaping process and appears to be uniform along the extent of the land surface. Thus, land 18 lies at angle A relative to the rim at each point along periphery 16. It is noted that proximal end 20 of window 14 is not provided with an angled land at all, thus resulting in portion 19 which is simply the end facing surface of the outer tube wall which is exposed by the cut forming window 14. The curvilinear profile of window 14 is best seen in FIG. 1 as comprising three sections: a first section 21 extending from the proximal end 20 of the window to a first predetermined point P1, and having a radius of curvature R1; a second section extending from point P1 to a predetermined point P2 adjacent the distal end of the window, this second section 22 having whatever blended radius of curvature R2 which is necessary to smoothly join the radiused section 21 to a third section 23 which is a linear portion extending at some angle B relative to axis 15. The window thus formed is best seen in FIG. 3 as having a relatively rectangular shape with rounded proximal and distal ends and generally parallel sides. Window 14 is formed by a process having at least two steps: a first step requiring passing a cutting tool through the distal tip of tube 10 along the curvilinear profile shown in FIG. 1 and a second step requiring the formation of land 18.

Figure 4:
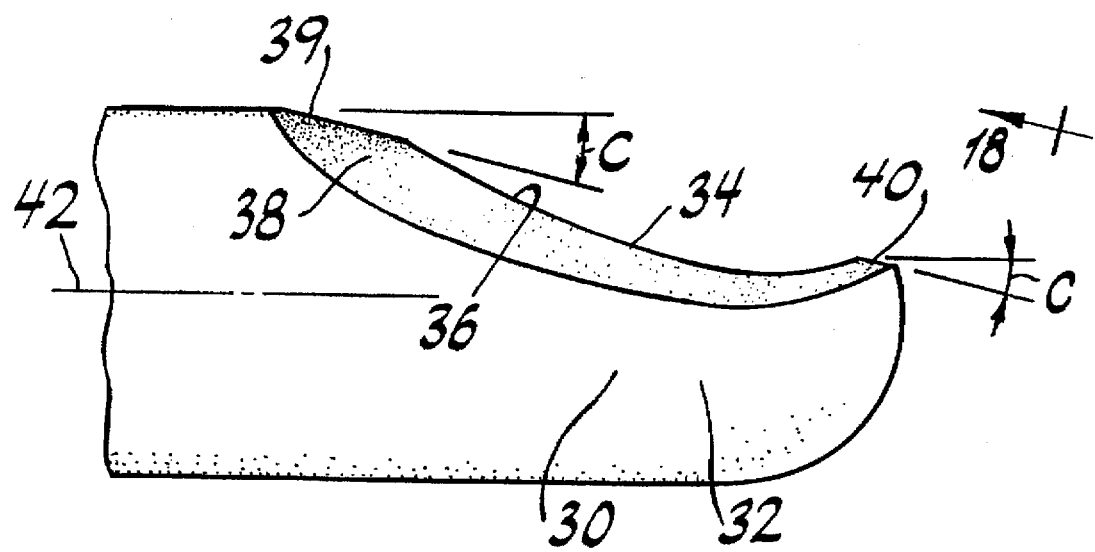
FIG. 4 is a side elevational view of a distal tip of an outer tube formed in accordance with the principles of this invention.
Figure 5:
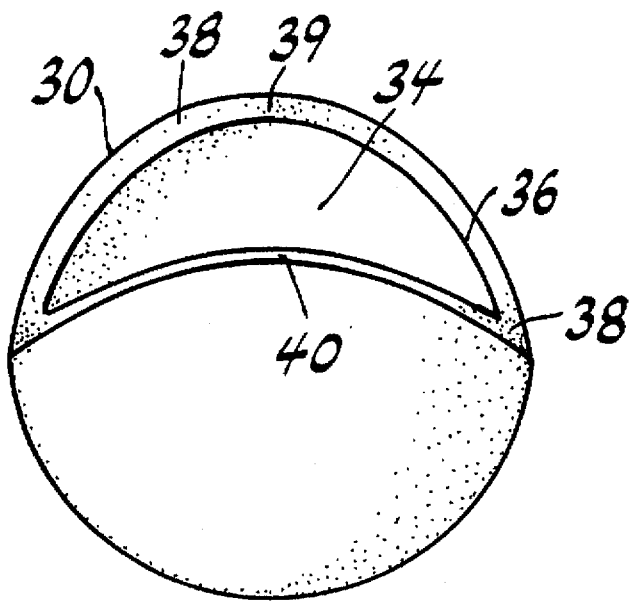
FIG. 5 is an end view of FIG. 4.
Figure 6:
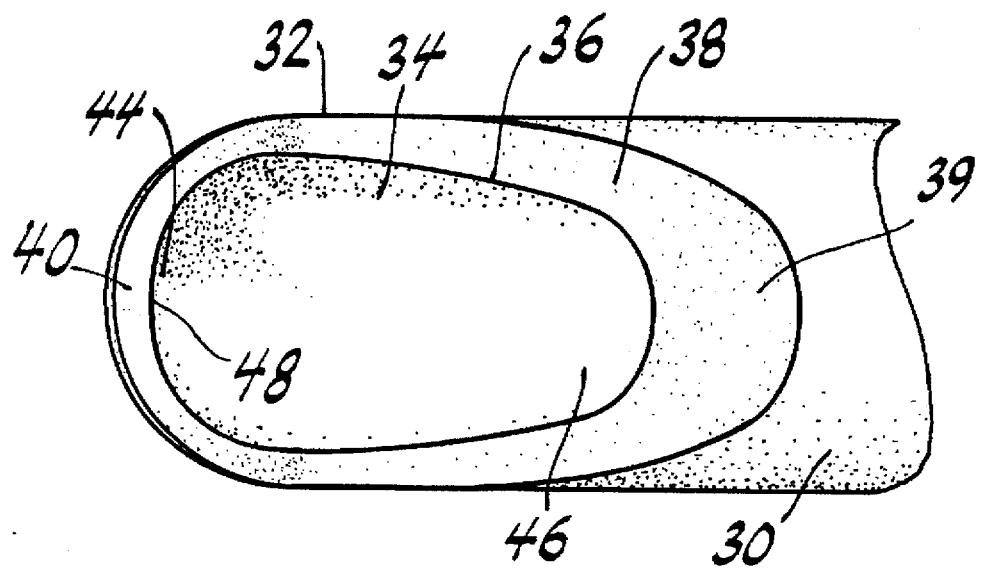
FIG. 6 is a plan view of FIG. 4.

The subject invention relates to an improved outer tube 30 and a process for forming the tube as shown in the remaining drawings. Referring to FIGS. 4 and 5, outer tube 30 has a distal end 32 provided with a curvilinear window 34 having a peripheral rim 36. The proximal end of tube 30 is conventional and forms no part of this invention. Window 34 is surrounded by a peripheral land 38 angled at its distal and proximal ends 39 and 40, respectively, at an angle C relative to the axis 42 of the outer tube. It will be noted that land 38 is, unlike the prior art embodiment discussed above, angled around the entire periphery of the window although points intermediate the distal and proximal ends 39 and 40 may be at angles other than angle C as will be understood below. As best seen in FIG. 6, window 34 is less rectangular than window 14 of the prior art embodiment and has more of a pear-shaped or generally elliptical outline with a large rounded distal end 44, a smaller rounded proximal end 46 and non-parallel sides. It should also be noted that the invention facilitates creation of a large window while maintaining a distal bearing tip 48 on axis 42. Tip 48 may act as a bearing surface against the exterior surface of the inner member.

Figure 7:
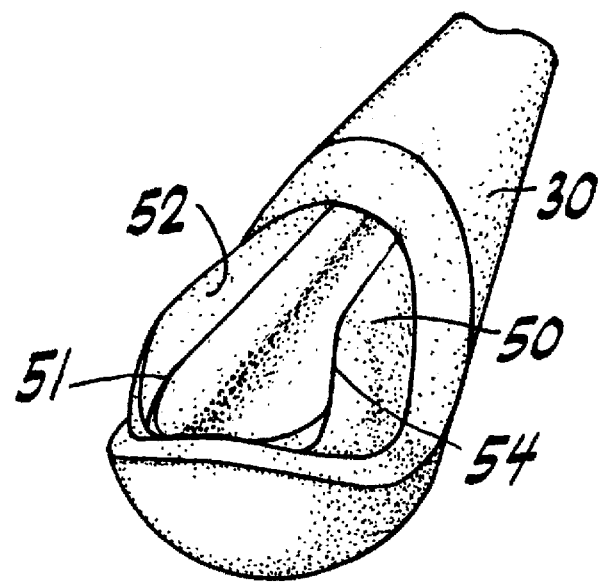
FIG. 7 is a front perspective view of the outer member shown in FIGS. 4–6 with a chosen inner member.
Figure 8:
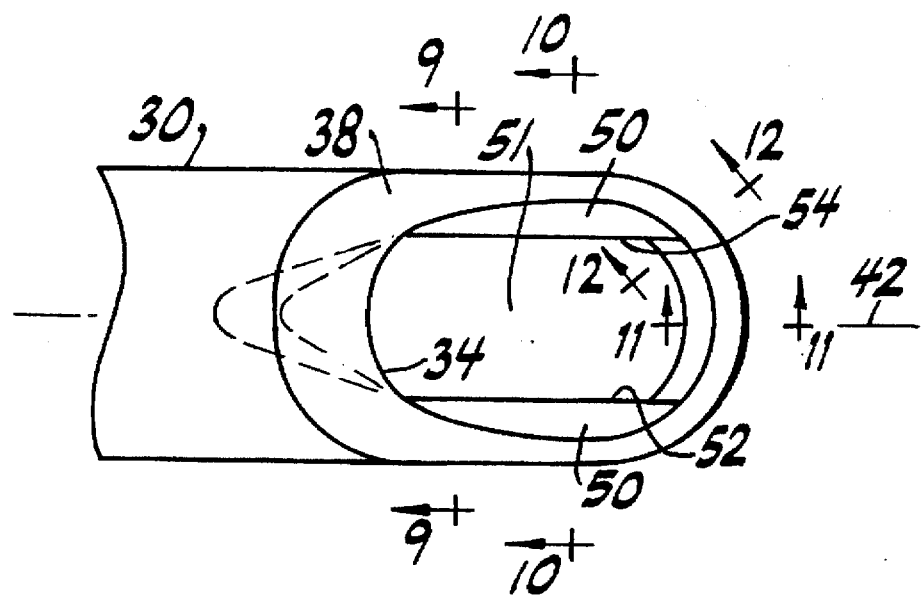
FIG. 8 is a diagrammatic plan view of FIG. 7.

FIG. 7 is a front perspective view of the distal tip of outer tubular member 30 assembled with an inner member 50 having a cutting window 51 although it will be understood that a variety of inner cutting window profiles could be used. To facilitate the explanation of the invention, FIG. 7 is presented in diagrammatic plan view in FIG. 8 showing the various points at which cross-sectional views shown in FIGS. 9 through 12 are taken.

Figure 9:
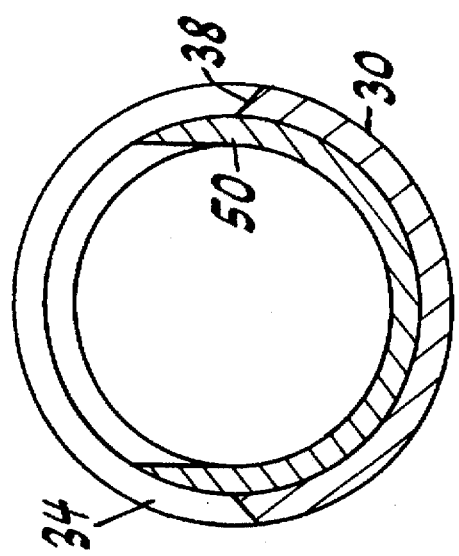
FIG. 9 is a sectional view of FIG. 8 taken along the line 9—9.
Figure 11:
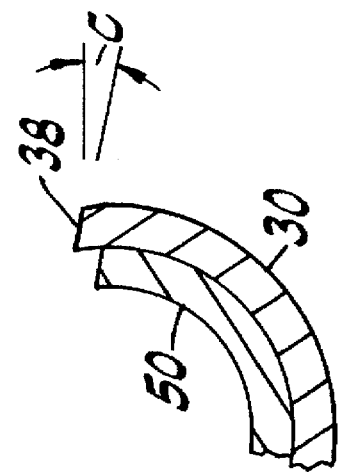
FIG. 11 is a sectional view of FIG. 8 taken along the line 11—11.
Figure 10:
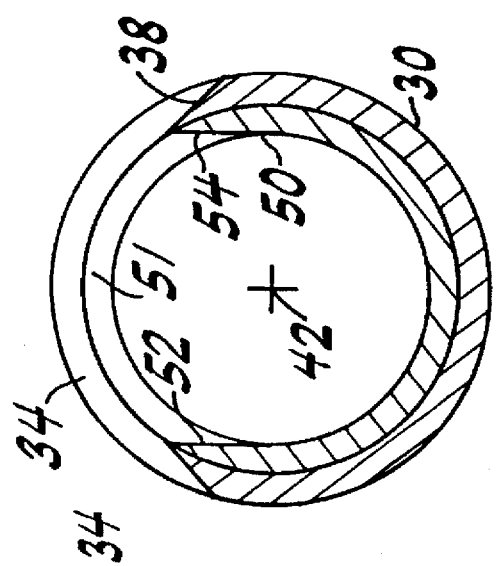
FIG. 10 is a sectional view of FIG. 8 taken along the line 10—10.
Figure 12:
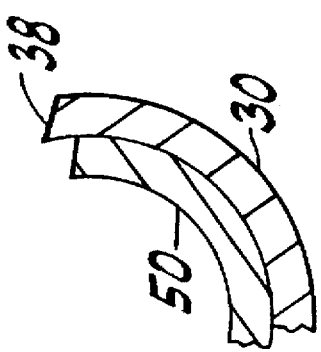
FIG. 12 is a sectional view of FIG. 8 taken along the line 12—12.
Figure 14:
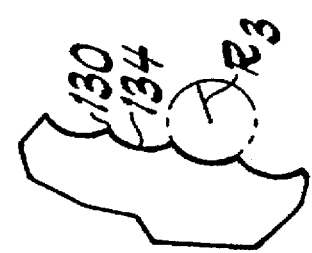
FIG. 14 is a sectional view of FIG. 13 taken along the line 14—14.

The particular form of cutting edge provided on inner member 50 has a pair of inwardly facing cutting surfaces 52 and 54 created on either side of inner window 51. Since each cutting surface 52 and 54 is close to if not exactly tangential with the interior surface of the inner tube (best seen in FIG. 10) and extends proximally from the distal tip of the inner tube, the inner window has a generally rectangular opening when viewed from the front. The inner window is formed, for example, by a wire EDM process in which the wire is longitudinally extending at a predetermined angle to the axis of the inner member and follows a generally rectangular path (viewed from the end of the tube). This path produces a tangential cutting surface at only certain points (i.e. at FIG. 10 but not at FIG. 9). The relationship of the cutting surfaces 52 and 54 relative to adjacent portions of outer window 34 is better seen by reference to FIGS. 9 through 12 which show sectional views through varying portions of FIG. 8. It will be noted that the angle of land 38 relative to a horizontal plane through axis 42 varies depending upon the longitudinal placement of the point on the land at which the angle is measured. Thus, as shown in FIG. 9, the edge of outer window 34 is fairly sharp because the wall of the outer tube is cut at a relatively low included angle compared to the angle of land 38 at other points, such as the point shown in FIG. 10. Similarly, the angle of land 38 at the point represented by FIG. 11 is different still and the angle shown in FIG. 12 is the angle C referred to above. It will be further noted that the relatively low included angle foxing the cutting edge of the inner cutting window, i.e. the intersection of surfaces 52 and 54 with the outside surface of inner member 50 results in a sharp edge in the areas of FIGS. 9 and 10. The curvilinear contour of outer window 34 in combination with the sharpness of its edges along rim 36 and the edges of the inner window produces efficient tissue resection.

Figure 13:
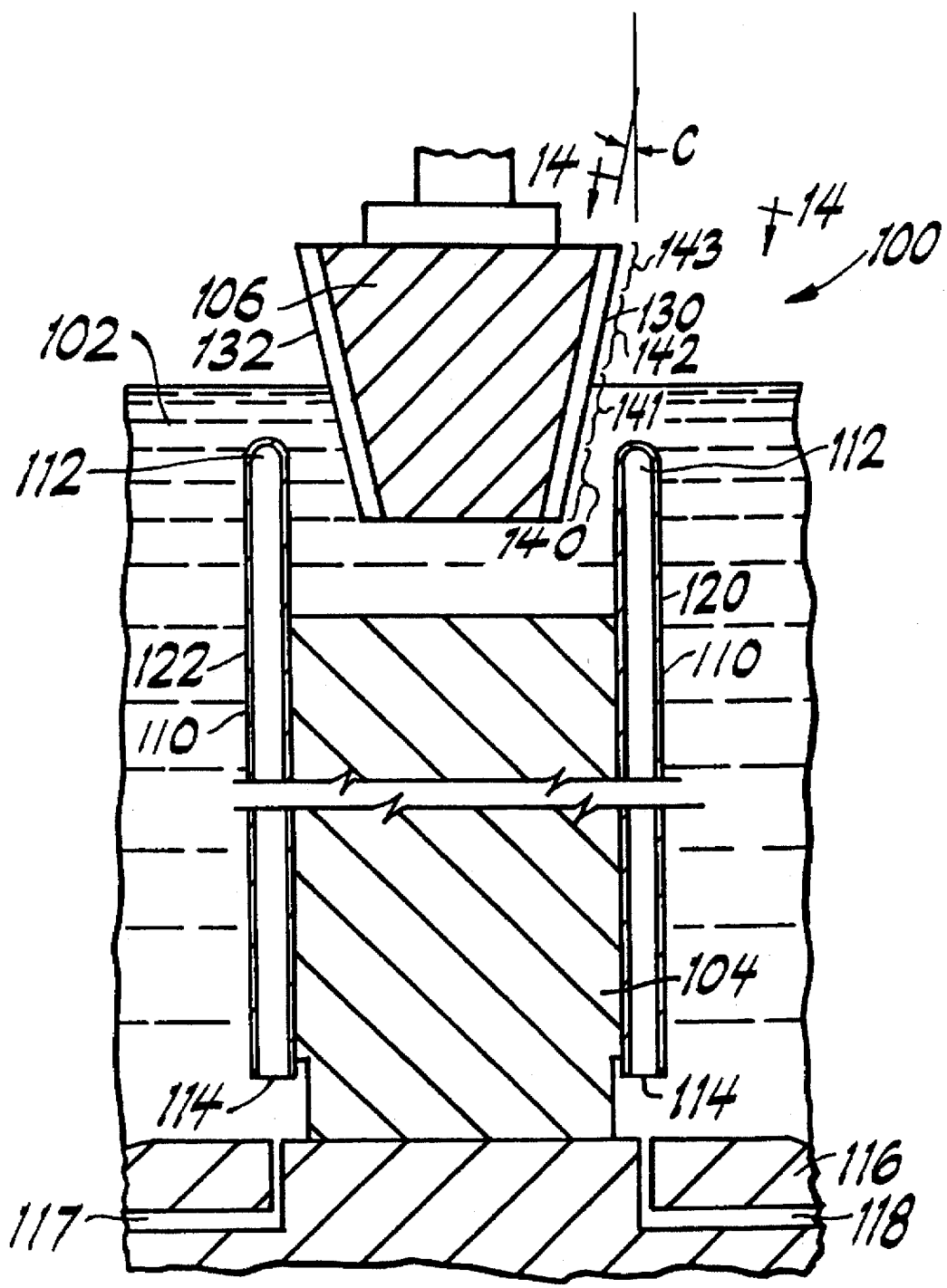
FIG. 13 is a diagrammatic elevational view in cross-section of an apparatus and method step incorporating the principles of this invention.

One process of foxing the curvilinear contour of window 34 at distal tip 32 is best understood by reference to FIGS. 13 through 18. The process utilizes a contouring apparatus such as an electrical foxing device capable of creating an arcuate surface in another body. The embodiment disclosed utilizes a plunge-type conventional computer numerically controlled (CNC) EDM device 100 incorporating a basin (not shown) for holding dielectric fluid 102, a work piece holder 104 and forming electrode tool 106 mounted to the EDM upper platen. A plurality of hollow outer tubes 110 are attached in a vertical orientation to opposite sides of holder 104, each outer tube having a closed top end 112 and an open bottom end 114. Holder 104 is attached to a base 116 mounted to the EDM lower platen, the base being provided with a plurality of fluid channels 117 and 118 aligned with the open ends of associated tubes 110. While only two tubes 110 are shown in FIG. 13, it will be understood that additional tubes are arranged on holder 104 in two parallel rows 120 and 122 which may extend perpendicularly to the plane of the paper. Similarly, tool 106 is an electrode having a trapezoidal cross-section, best seen in FIG. 13, extending perpendicularly to the plane of the paper and above holder 104. The angled sides 130 and 132 of tool 106 are each provided with a plurality of parallel channels 134 having arcuate profiles oriented at angle C relative to the axes of the tubes in rows 120 and 122, each having a radius of curvature R3, best seen in FIG. 14, which ultimately interacts with outer tubes 110 to create the unique profile of window 34. It will be understood that the channels could have other than circular profiles.

Figure 15:
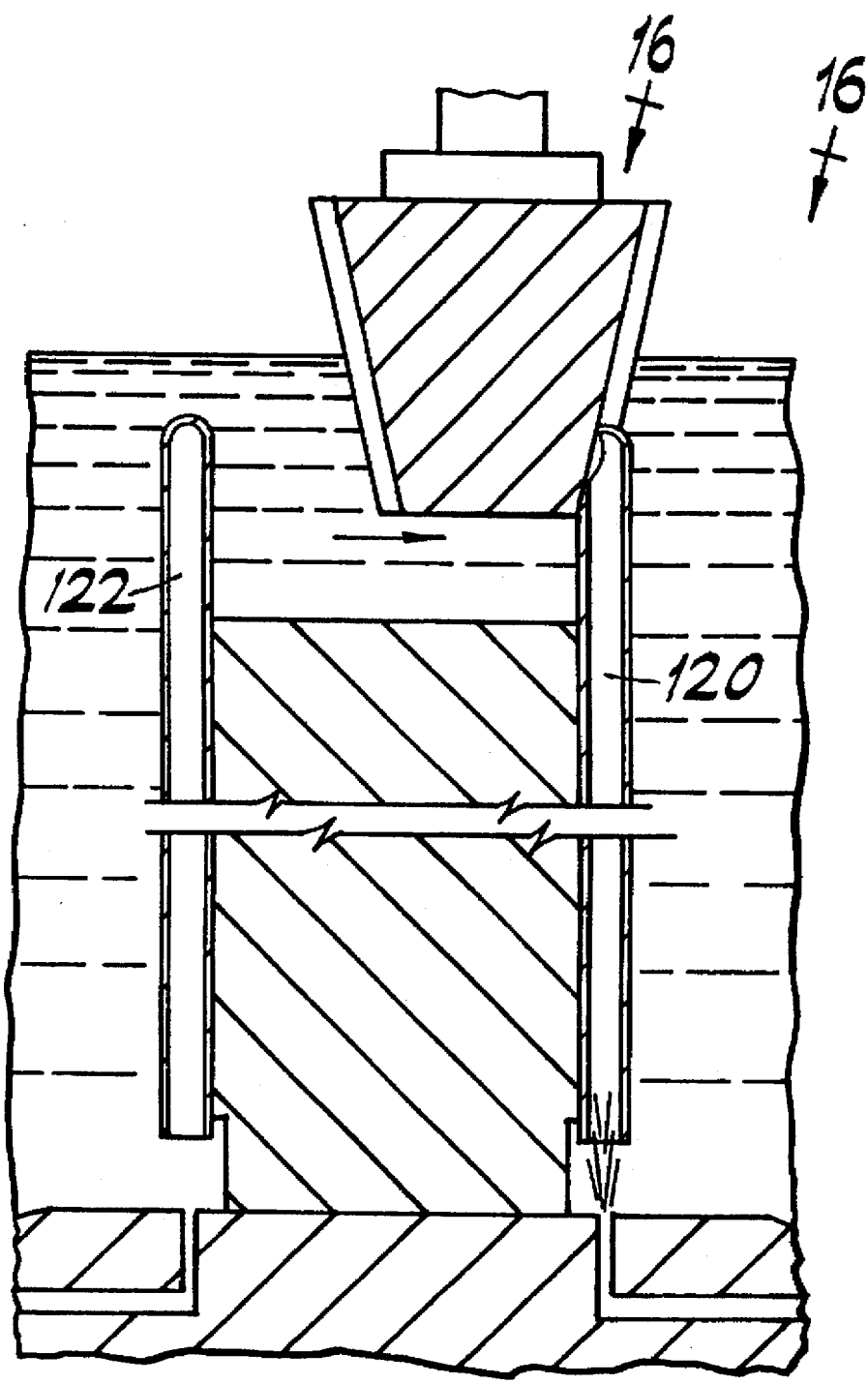
FIG. 15 is a view of the method and apparatus of FIG. 13 in a different stage of the process of this invention.
Figure 17:
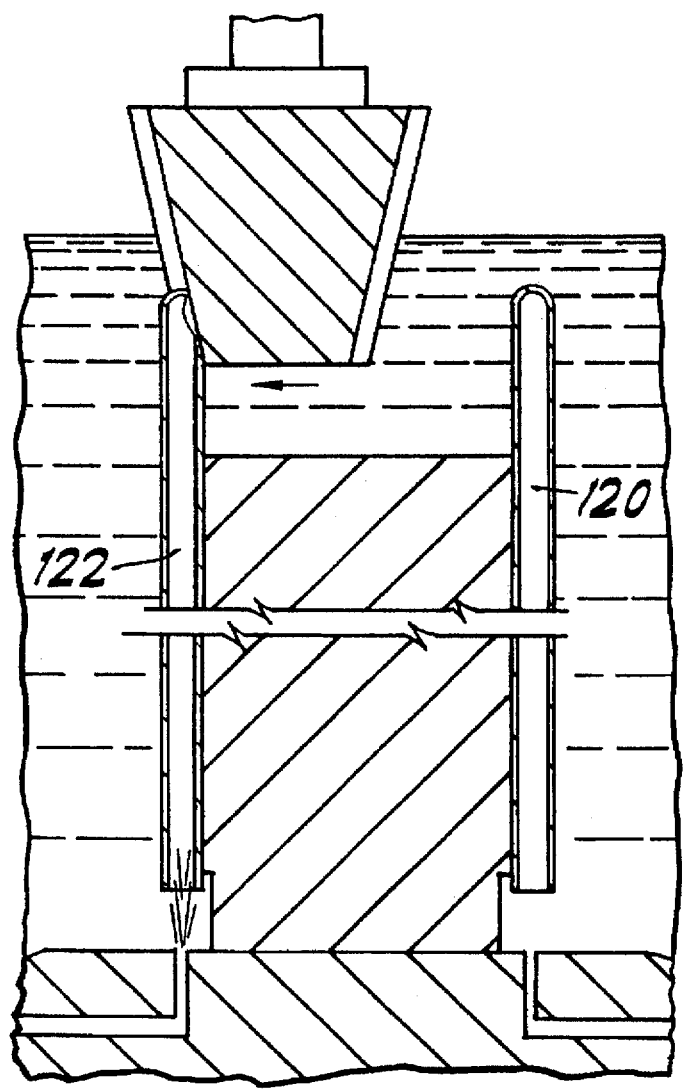
FIG. 17 is a view of FIG. 15 taken at a different stage in the process of the invention.

As shown in FIG. 15, electrode tool 106 is first moved down to a selected level between the parallel rows 120 and 122 of outer tubes 110 and then laterally toward one of the rows, the rate being determined by the machine control parameters in order to have the distal tip of outer tubes 110 contact a selected channel 134. While a plurality of channels are provided on each surface 130 and 132, not all portions of all channels need to be used at any one time and the tool may be shifted around by proper programming of the CNC machine to utilize selected portions of the channels and selected channels as will be understood below. For example, any given channel 134 may be thought of as having a plurality of adjacent sections 140, 141, 142 and 143. The vertical positioning of electrode 106 could be, for example, set to have lower-most section 140 be the active section. As the electrode continues to move laterally a predetermined distance to a selected point, the EDM process forms an opening in each of the outer tubes while dielectric fluid is flushed through channels 118 and out the opening created at the distal tip. During machining, electrical discharge parameters are modified under program control so as to minimize cycle time while maintaining acceptable surface finish and edge sharpness on the finished product. The pressurized dielectric fluid introduced by the timed flushing port reduces the machining time by removing swarf from the machining zone. The opening is defined by the intersection of the cylindrical tube wall at the rounded, closed end of the tubes with the arcuate profile of channels 134.

When the tool has been moved laterally a programmed distance to form the desired window 34, the direction of the tool is reversed to approach row 122 and the channels along surface 132 are brought into engagement with the outer tubes in row 122 in order to produce the chosen profiles in those tubes.

Figure 18:
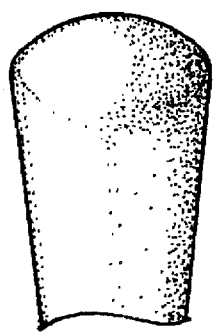
FIG. 18 is an end view of FIG. 4 taken along the line 18—18 showing the profile of the tip viewed along a line angled relative to its axis.

It will be appreciated by those skilled in the art that while tool 106 has a relatively simple shape and moves in a relatively simple pattern, the intersection of the tool with the outer tube produces a resultant complex profile. Rather than being defined by a complex shape requiring several processing steps for its formation, window 34 has a simple arcuate profile when viewed in FIG. 16, or better still, when viewed along a line at an angle C to the tube axis as best seen in FIG. 18. The intersection of the arcuate channel profile with the cylindrical tube results in cutting edges with low included angles thereby making a subsequent sharpening operation unnecessary. The shape of the surface of any given land 38 surrounding rim 36 and the shape of the associated actual window 34 may be considered as being defined by the locus of all points lying at the intersection of an elongated, transversely arcuate surface with the cylindrical body of the tube oriented at a predetermined angle relative to the transversely arcuate surface. Put another way, the definition of the perimeter of window 34 may be thought of as the intersection of a cylindrical body with an imaginary surface having a predetermined, symmetrical, concave arcuate profile. In practice this imaginary surface is defined by the concave surface of channel 134 and is considered endless because the surface extends entirely through the cylindrical body enough to form a window therein. In the preferred embodiment, however, the activatable sections (140, etc.) of the surface of channel 134 lie on this imaginary surface and need only subtend a lateral or transverse distance approximately greater than or equal to one-half the outside diameter of the cylindrical body in order to form land 38. If the imaginary surface is linearly extended in a direction which is aligned with the axis of the tube, and if the arcuate profile transverse to the axis is a simple concave radius, the resultant locus of points defines convex land 38 (complementary to the concave radius). If some other orientation or profile is used, the locus of points will produce a different shape.

Figure 16:
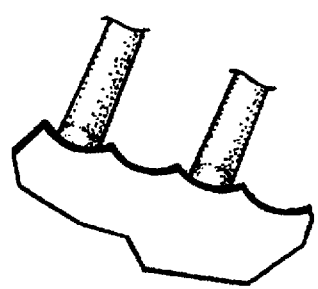
FIG. 16 is a sectional view of FIG. 15 taken along the line 16—16.

The transverse curvature of window 34 when viewed as shown in FIG. 16 is the same as that shown in FIG. 18. While the arcuate profiles of channels 134 are at a constant radius of curvature along the length of the channels, it will be understood that the radius of curvature may vary along the channel length and/or the arcuate surface may have a contour other than circular extending along the axis line.

Because the shape is two-dimensional when viewed axially to the cylindrical surfaces 130 and 132 of the tool, complex shaped tooling or simultaneous programmed machine motions are not required. The shape of the tool may be machined by using CNC wire EDM, or produced by conventional or electrochemical grinding using a wheel onto which the proper radius has been dressed. Similarly, plunge type EDM or ECM may be used with the part contour being produced by contours on the tooling. Tooling cost is low due to the simple profile and, because complex machine motions are not required, simultaneous multiple part machining is readily implemented.

Figure 19:
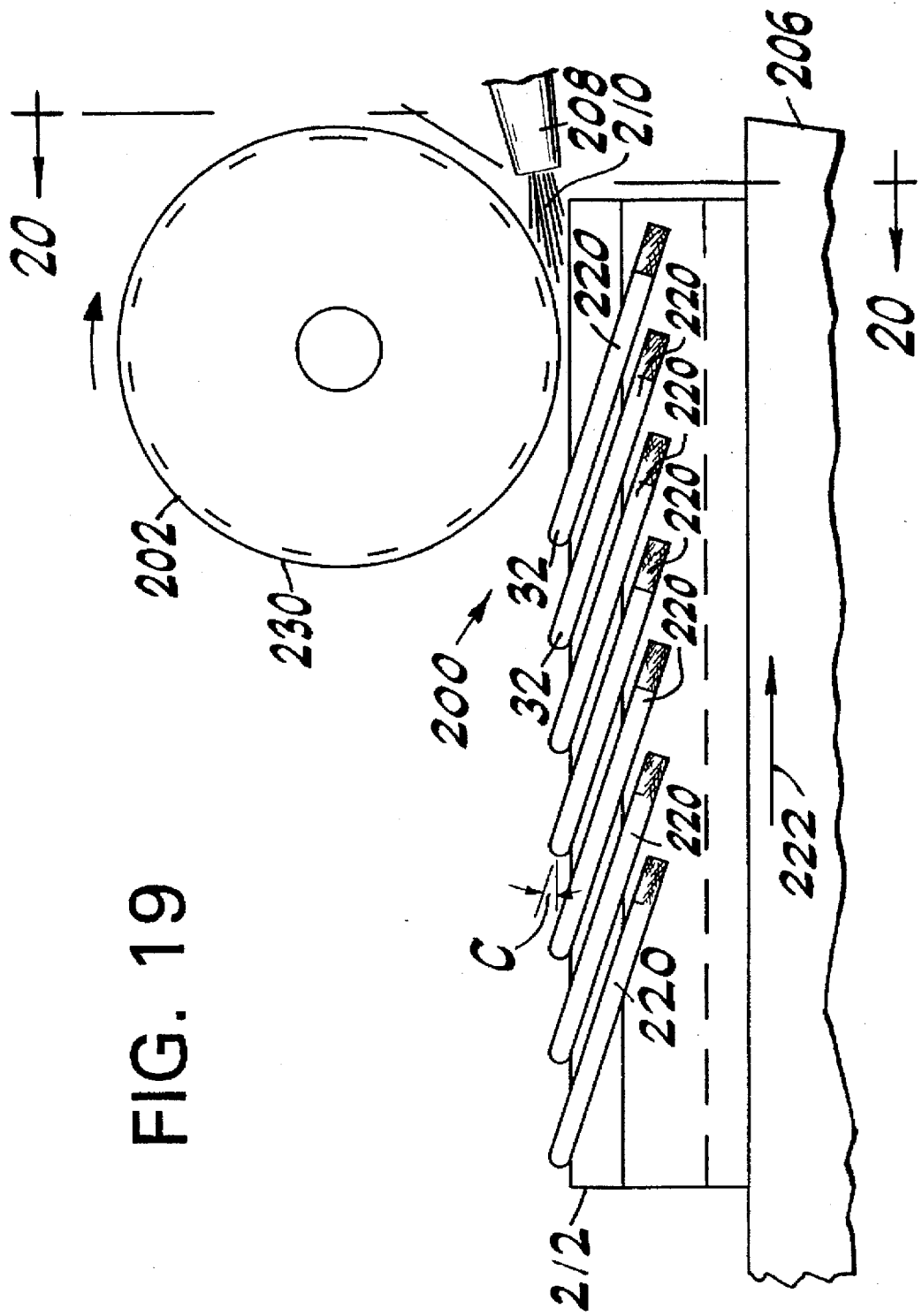
FIG. 19 is a diagrammatic front elevational view of an electrochemical grinding apparatus used in a preferred embodiment of the invention.
Figure 20:
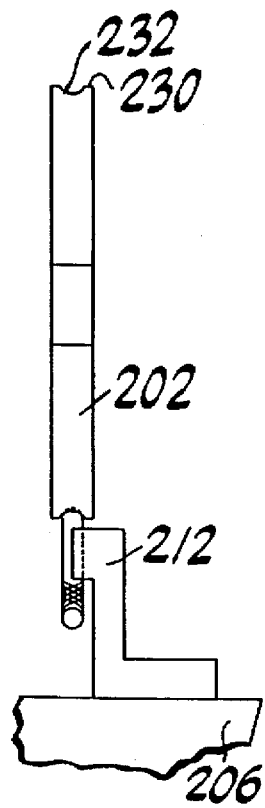
FIG. 20 is a view of FIG. 19 taken along the line 20—20.
Figure 21:
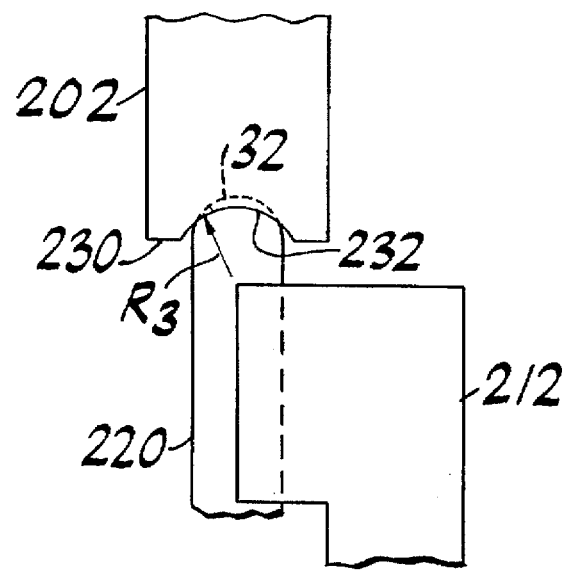
FIG. 21 is an enlarged view of a portion of FIG. 20.
Figure 32:
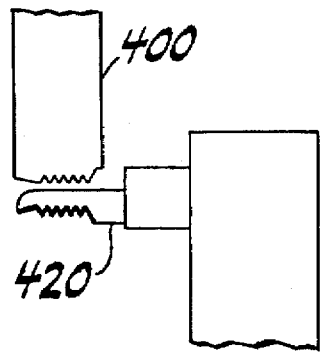
FIG. 32 is a view of FIG. 31 at a different portion of the method.

A preferred process of forming the curvilinear contour of window 34 at distal tip 32 is best understood by reference to FIGS. 19–21. This process utilizes a cylindrical forming apparatus which, in the preferred embodiment, is a conventional electrochemical grinding machine (ECG) which has had the perimetral (circumferential) surface of its abrasive grinding wheel shaped to ultimately form the contour of window 34. It will be understood that the processes disclosed herein could be used to form an opening in a previously closed distal end of a tubular member, or could be used to shape or sharpen an opening previously formed therein.

Electrochemical grinding machine 200 comprises a grinding wheel 202, a base (not shown) for supporting a table 206 movable relative to the base and wheel under programmable control. A nozzle 208 directs electrolyte 210 at the work location adjacent wheel 202 in a conventional manner. The operation of the machine components, processes, table motion, speed, etc. is controlled in a conventional manner. Table 206 receives a jig 212 to hold a plurality of tubular members 220 in an inclined orientation relative to a line tangent to wheel 202. The tubular members 220 are electrically conductive and serve as one electrode within the apparatus (the wheel acting as the other electrode). Each member 220 has a closed distal tip 32 into which a window 34 (as shown in FIGS. 4–6) will be formed as explained herein. The tubular members 220 are inclined at an angle C which is the same as the angle between the tubular axis and the face of the channels of tool 106 as shown in FIG. 13. As table 206 moves in direction 222 the distal tips of successive tubular members 220 will move tangentially past wheel 202. Perimetral surface 230 of wheel 202 is provided with a groove 232 having the selected profile which in this embodiment is a simple radius of curvature R3, the same radius as that of channel 134 shown in FIG. 14. Groove 232 is best seen in FIG. 21 which shows a view of the wheel groove within essentially a radial plane of the wheel. Moving table 206 along a linear path of motion in the plane of wheel 202 to tangentially intersect distal tips 32 of tubular members 220 with the groove at the wheel periphery during activation of the electrochemical process will produce in each tip a curvilinear window 34 as shown in FIGS. 4–6 and 18 without any additional shaping or sharpening process. While jig 212 and table 206 are shown in the drawings to fixedly hold each tube in a fixed orientation relative to wheel 202, as will be explained below the tubes could be supported on jig 212 in a movable manner and the table could move along a complex path of motion (other than simply in one linear direction). The movement of the tubes relative to the jig or the movement of the table relative to the base could be continuous or indexed (to discrete positions) under programmable control. While the apparatus of FIGS. 19-21 utilizes electrochemical grinding, similar wheel shapes and motions may be applied to conventional grinding or other processes.

While the device and process disclosed have been described in terms of an outer, stationary tubular member, it will be understood by those skilled in the art that the cutting edge of an inner, rotating tubular member may also be formed in accordance with the principles of the invention disclosed herein. Appropriate changes may be necessary in the shapes and sizes of the electrode tool 106 or the wheel 202, supporting jigs and paths of travel, depending upon the desired shape of the inner cutting edge. One such device and process is disclosed below in FIGS. 37 and 38.

Furthermore, the window shape of the preferred embodiment of the outer tube disclosed herein is such that a linear tangential motion of the inclined tubular members 220 relative to wheel 202 is the desired motion to produce the desired shape. Variations in window shape or cutting edges in either the inner or outer members may rewire other orientations of the tubular members or other than linear motion of table 206.

Also, as briefly mentioned above, the path of motion of the tubes relative to the wheel may change depending upon the desired shape to be formed in a tubular member. For example, the tube may be moved in varying directions other than linear and/or it may be rotated about its axis as it moves past the wheel, moved up and down relative to the wheel on any given pass to change the depth of the cut in the tube, etc. Additionally, the machine could have different ECG stages, each with a different wheel so that a complex table path of motion would pass differently shaped wheels to produce complex cuts and different shapes. Another example may be a tube formed by a plurality of linear passes. That is, the tube could be moved linearly relative to a wheel as described above, rotated about its axis, moved linearly again, rotated again, moved again, etc. The wheel in such case could even have a flat peripheral surface to produce an opening approximating window 34. With appropriate indexing and motion of the tubular member in all dimensions relative to the jig (e.g. linearly along its axis, rotating about its axis and about another axis transverse to its axis) and with appropriate indexing and motion of the table relative to the wheel (or relative to different wheels if additional stages are used), it would be possible to produce cuts of almost any imaginable shape, depth, angle and length such that this method would even make it possible to produce cutting teeth in the tubular member. This latter method could be analogous to creating a complex shape by a CNC (computer numerical control) milling machine operating with several degrees of freedom and would result in a toothed opening in either an inner or outer tubular member of a rotating surgical shaver.

Figure 22:
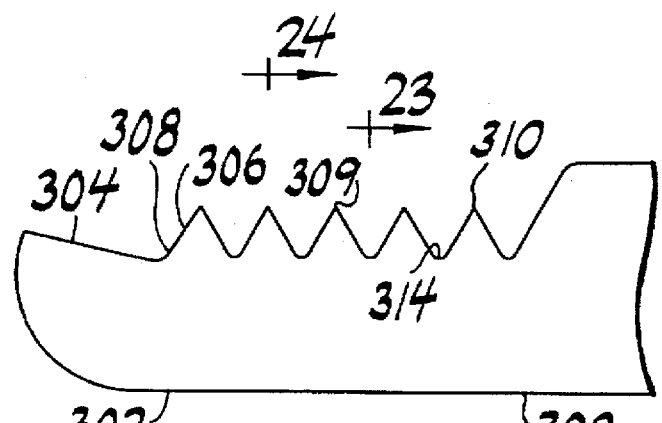
FIG. 22 is a side elevational view of the distal end of a prior art toothed outer member.
Figure 24:
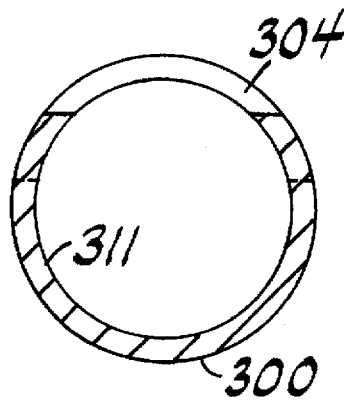
FIG. 24 is a cross-sectional view of FIG. 22 taken along the line 24—24.
Figure 23:
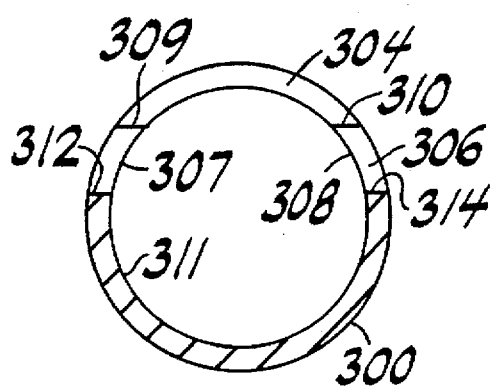
FIG. 23 is a cross-sectional view of FIG. 22 taken along the line 23—23.

One method of forming the cutting teeth in a tubular member is shown in FIGS. 22 through 36. As shown in FIGS. 22–24 a prior art outer tubular member 300 has a distal tip 302 comprising a cutting window 304 bounded a plurality of teeth 306 in two, parallel and longitudinally extending rows 307 and 308. The cutting window and teeth of such an outer tubular member 300 may be formed, for example, by a conventional EDM process in which the cut is made transversely through the distal tip of the tubular member so that the top edges 309, 310 of teeth in opposing rows 307, 308 are coplanar at corresponding transverse points and the troughs 312 and 314 between adjacent teeth in opposing rows are also coplanar. The included angle of each tooth is bounded by the horizontal surface 309 (or 310, depending on the row) and the inner surface 311 of the tube.

Figure 25:
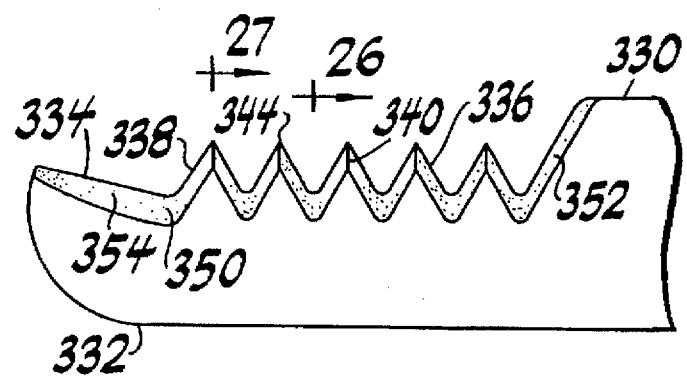
FIG. 25 is a side elevational view of the distal end of an outer tubular member constructed in accordance with the principles of this invention.
Figure 27:
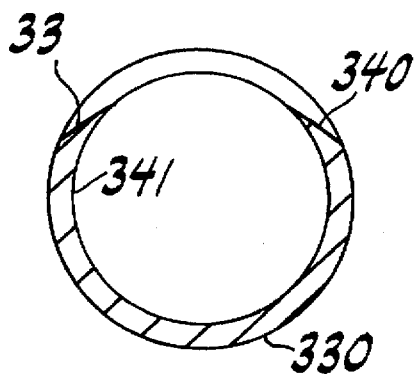
FIG. 27 is a cross-sectional view of FIG. 25 taken along the line 27—27.
Figure 26:
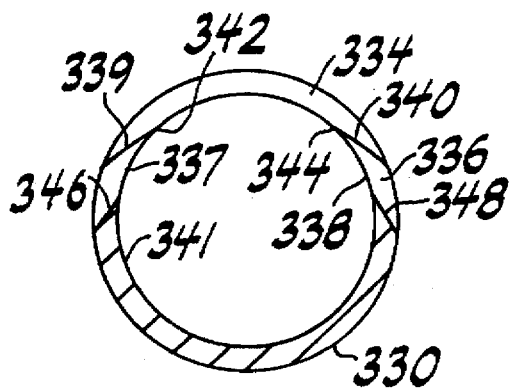
FIG. 26 is a cross-sectional view of FIG. 25 taken along the line 26—26.

As shown in FIGS. 25 through 27 outer tubular member 330 constructed in accordance with the principles of this invention has a toothed profile considerably sharper than that of prior art tubular member 300. Outer tubular member 330 has a distal tip 332 in which a cutting window 334 is formed which is bounded by a plurality of teeth 336 in two, parallel and longitudinally extending rows 337 and 338. As with the prior art device, the teeth 336 in one row are transversely coplanar with the corresponding teeth in the opposite row. The top edges 339 and 340 of each tooth 336 are curved to produce points 342 and 344. Troughs 346 and 348 between adjacent teeth are also curved but at a different profile as will be understood below. The included angle between edge 339 and the inner surface 341 is smaller than the corresponding angle of the prior art device 300.

Cutting window 334 has a land 350 entirely surrounding the window, the land being angled relative to the window periphery so that there is a sharp edge on the radially innermost side adjacent to the opening. The included angle between the land surface and the inner surface 341 varies depending upon the longitudinal position of the point where the angle is measured. For example, the included angle at edge 339 is smaller than that at trough 346. Land 350 comprises a proximal land section 352 and a distal land section 354, the shapes of which are shown diagrammatically. It will be understood that, while an inclined land surface will surround window 334, the actual shape of this land may vary from that shown in FIG. 25 depending upon the actual tool used.

FIGS. 28–33 and 36 show an apparatus and method for producing the toothed outer tubular member 330. Wheel 400 and jig 402 are part of electrochemical grinding machine similar to that shown in FIG. 19. The remaining components (table, electrolyte nozzle, etc.) are omitted for clarity. Wheel 400 has a predetermined thickness 404 and a predetermined perimetral surface 406 which is dressed with a plurality of notches 408 and proximal and distal angled surfaces 410 and 412, respectively, to form the various teeth 336 and proximal and distal land sections 352 and 354 as will be understood below. The shapes of surfaces 410 and 412 in combination with the motions of various components will affect the shape of proximal and distal land sections 352 and 354. The various cuts in the perimetral surface 406 have a radially outermost portion (extent) 416 and a radially innermost portion (extent) 417. The shape of the perimetral surface may be changed to produce a variety of cuts in a workpiece 420 as will be understood below.

Figure 30:
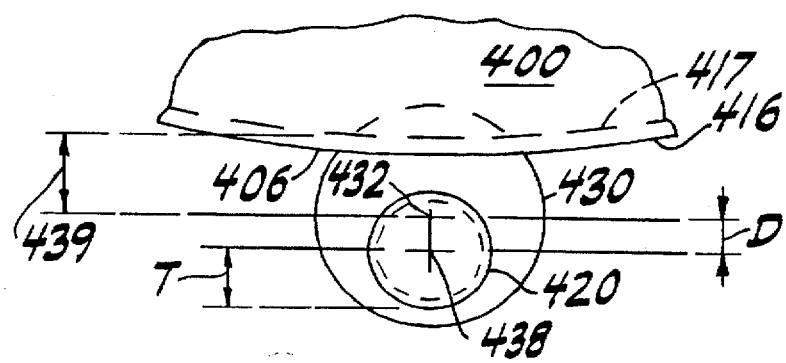
FIG. 30 is an enlarged view of a portion of FIG. 29.
Figure 28:
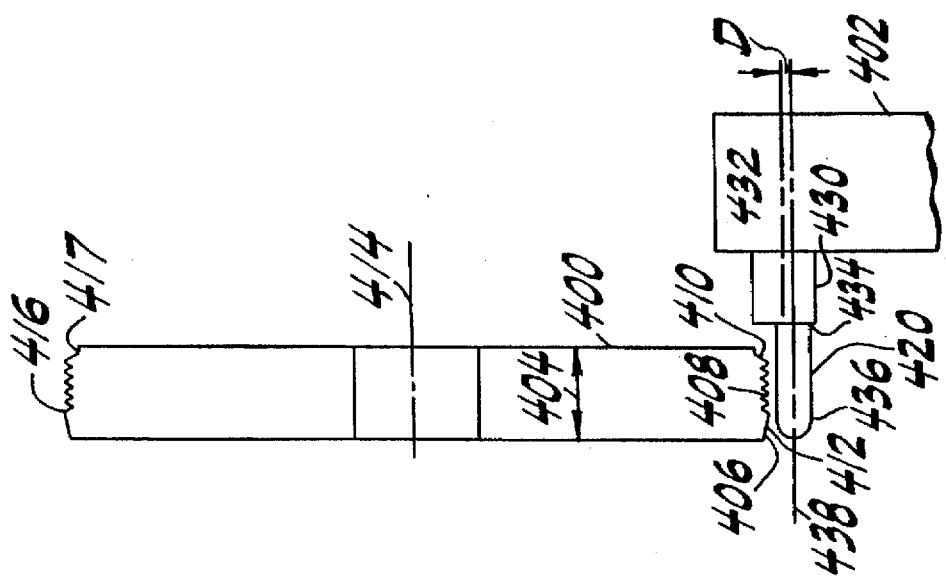
FIG. 28 is a side elevational view of an apparatus used in the method of producing a toothed outer such as that shown in FIG. 25.
Figure 29:
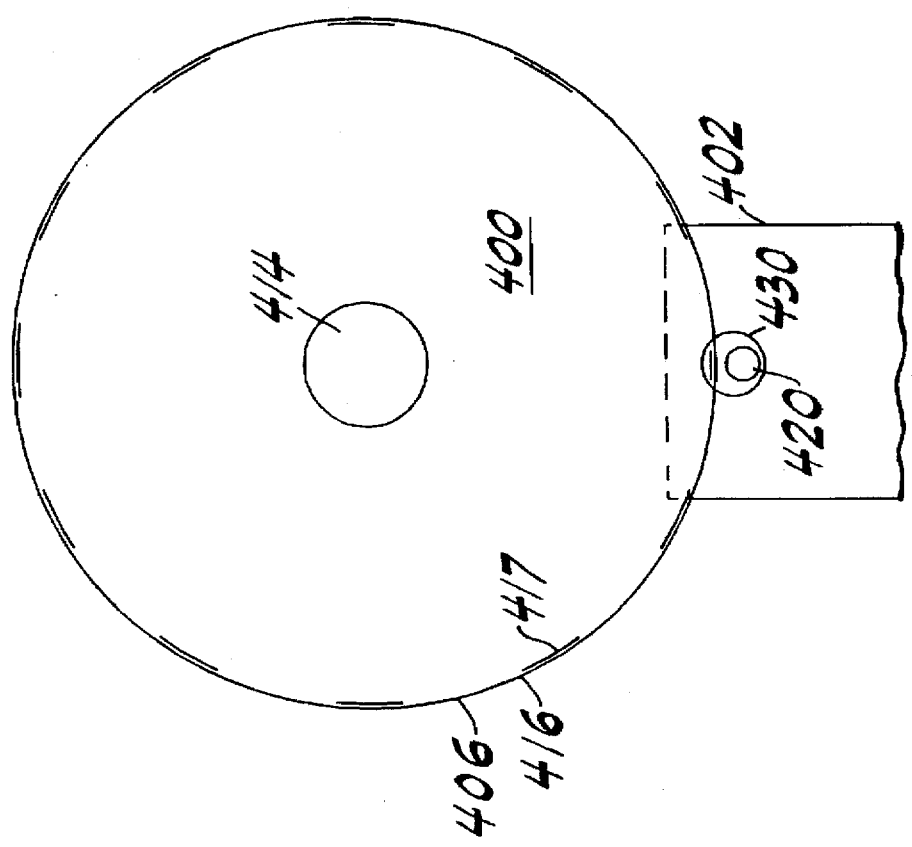
FIG. 29 is a front elevational view of FIG. 28.
Figure 31:
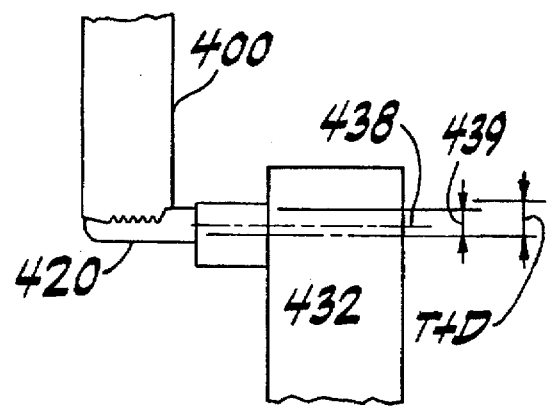
FIG. 31 is a side elevational view of the components of FIG. 28 showing a portion of the method of producing the toothed outer member of FIG. 25.
Figure 33:
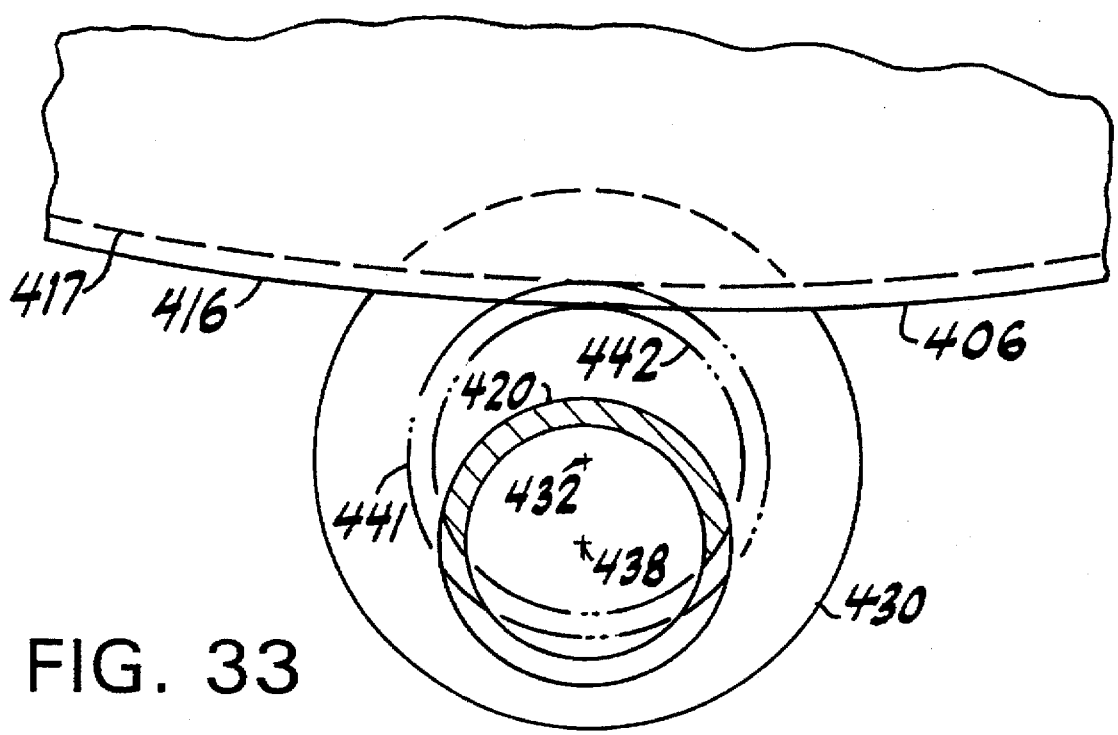
FIG. 33 is an exploded view of FIG. 30 showing in phantom the path followed by various portions of the outer tubular member during the manufacturing process.
Figure 34A:
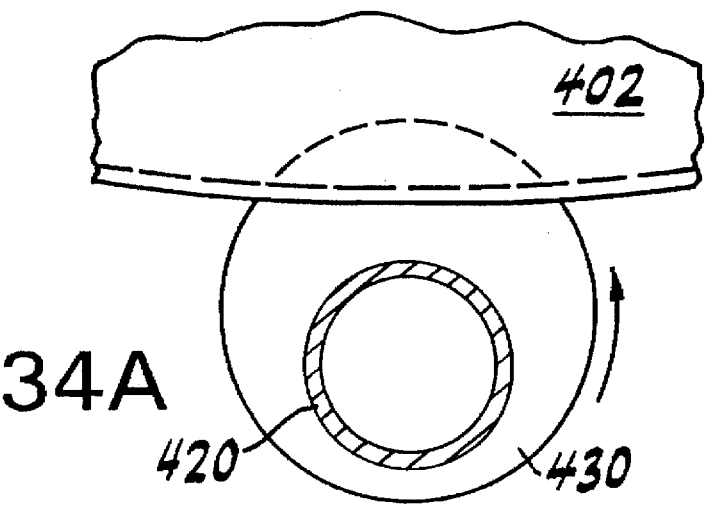
FIGS. 34a through 34g show various positions of the components of the invention during various portions of the method used to form the toothed outer tubular member.
Figure 34B:
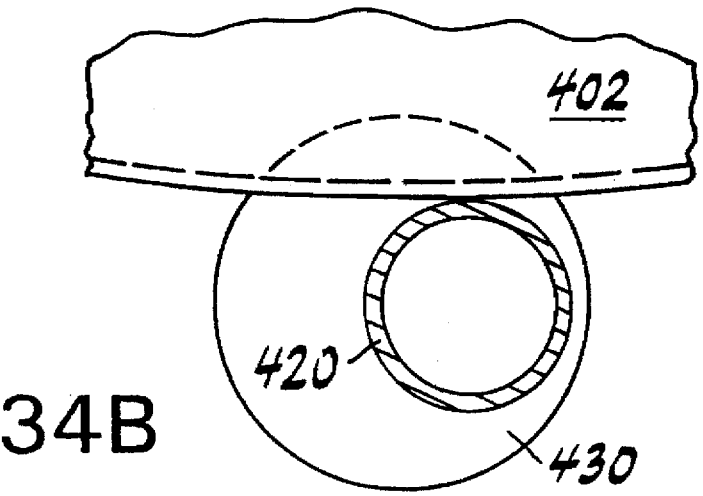
Figure 34C:
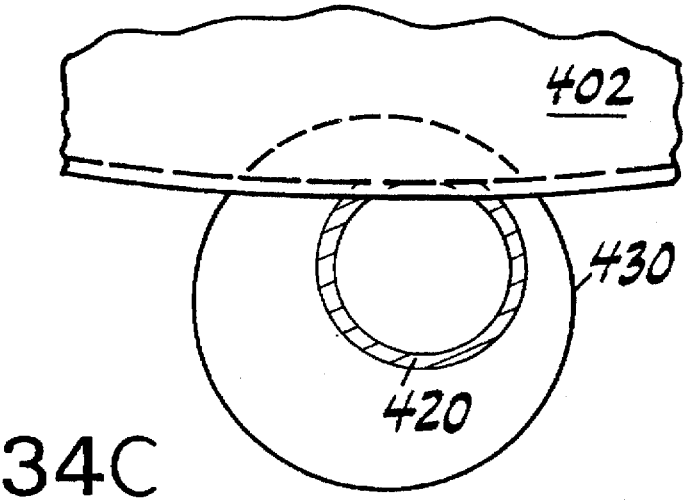
Figure 34E:
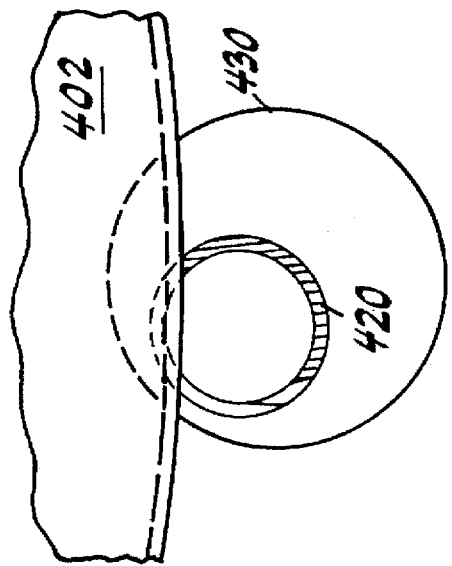
Figure 34G:
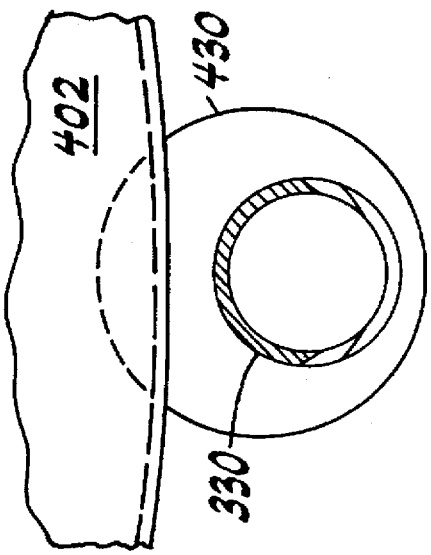
Figure 34D:
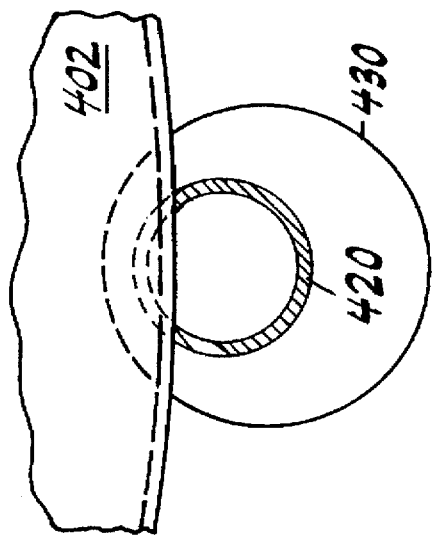
Figure 34F:
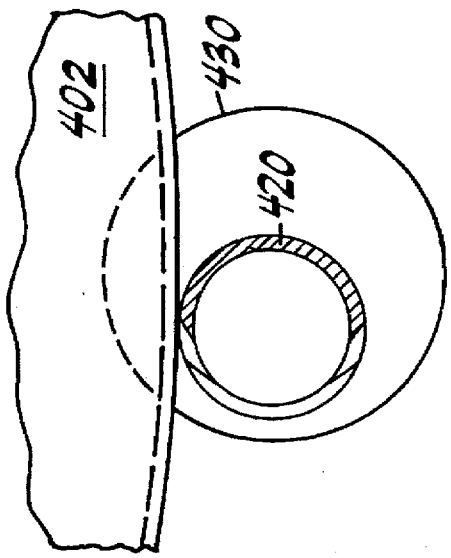

Jig 402 supports a rotatable housing 430 which is adapted to rotate about an axis 432 parallel to wheel axis 414. Extending from the front face 434 of housing 430 is a tubular workpiece 420 which has a distal tip 436 and an axis 438 which is aligned parallel to and offset by a distance D from axis 432 as best seen in FIGS. 28 and 30. The distance 439 between axis 432 and the radially innermost portion 417 is less than the sum of the radius T of the tubular member and the distance D between the tubular member axis 438 and housing axis 432. Wheel 404 is adapted to rotate about fixed axis 414 while the workpiece 420 is adapted to move in an eccentric pattern about axis 432. As shown in FIGS. 29–33, the workpiece does not rotate about its axis 438 but rotation of housing 430 about axis 432 causes the workpiece axis 438 to be placed at variable radial distances from the wheel axis 414 such that different parts of the workpiece 420 will intersect the perimetral surface 406 of the wheel at different points. The eccentric motion of workpiece 420 about axis 432, as best seen in FIG. 33, causes points at varying radial distances from axis 432 to rotate along different circular paths. Thus, the circular path 441 is that defined by points on workpiece 420 that rotate about axis 432 at a radial distance from axis 432 equal to the distance between axis 432 and innermost portion 417 of the wheel's perimetral surface. Similarly, the circular path 442 is defined by points on workpiece 420 that rotate about axis 432 at a radial distance from axis 432 equal to the distance between axis 432 and outermost portion. 416. It will be understood that various parts of the workpiece rotate along curvi-linear paths, in this case circular paths having radii between paths 441 and 442. As shown in FIGS. 34a–g the rotation of workpiece 420 relative to wheel 402 proceeds in various stages until ultimately, in FIG. 34g, an outer tubular member 330 is produced.

Figure 35A:
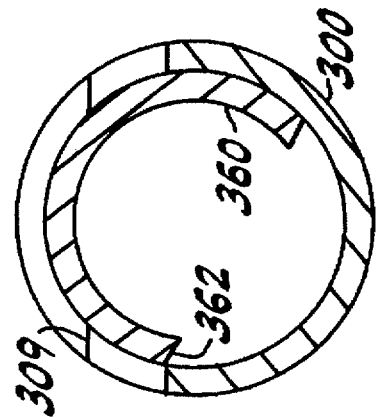
FIGS. 35a and 35b show cross-sectional views of a prior art rotatable surgical shaver having an outer tubular member such as that shown in FIGS. 22–24 and an inner tubular member having a cutting window formed by a straight cut.
Figure 35B:
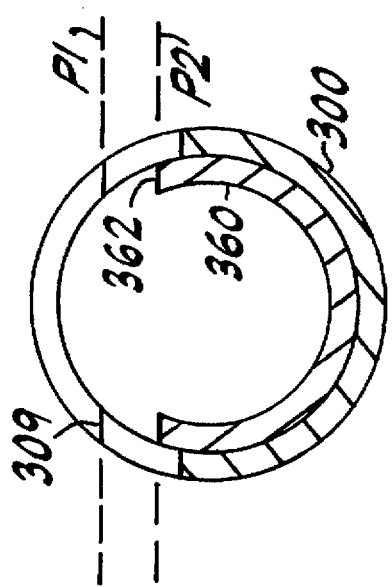

The sharper teeth of an outer tubular member that can be easily produced with this method produce a sharper rotatable surgical shaver. As shown in FIG. 35, a prior art surgical shaver comprising an outer tubular member 300 and inner tubular member 360 is limited in sharpness. Outer tubular member 300 is identical to that shown in FIGS. 22–24. Inner tubular member 360 is shown also with a straight cut through its cutting window so that all of the cutting surfaces lie in parallel planes P1 and P2 (parallel to the plane of the inner window), as best seen in FIG. 35a. (Note that a sharper inner member 50 is shown in FIGS. 8–11 with cutting surfaces 52 and 54 in parallel, longitudinal planes which are perpendicular to the inner window. Member 50 could be combined with outer member 300.) When inner member 360 is rotated relative to the outer member 300, the movement of cutting surface 362 past cutting edge 309 creates a shearing action. The actual cut occurs at the junction of the radially innermost portion of edge 309 and the radially outermost edge of surface 362. Because of the straight cuts used to form the cutting windows of such prior art devices, the included angle of these edges is large and, therefore, their sharpness is limited.

Figure 36A:
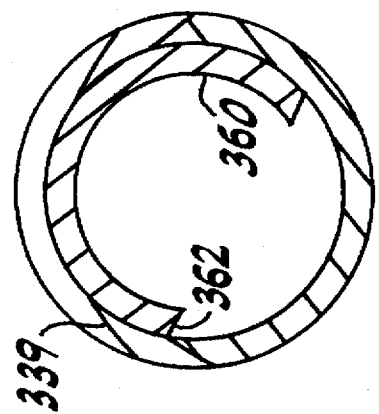
FIGS. 36a and 36b are cross-sectional views of a rotatable surgical shaver utilizing an outer tubular member constructed with the principles of this invention and a prior art inner tubular member having a cutting window with a straight cut.
Figure 36B:
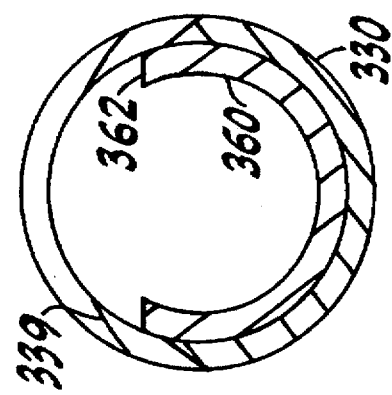

On the contrary, as shown in FIG. 36, simply replacing a conventional outer member 300 with an outer tubular member 330 constructed in accordance with the principles of this invention will increase the sharpness of the junction between the radially innermost portion of edge 339 and the radially outermost edge of surface 362 thereby producing a smaller included angle and a sharper cut. It will be understood that inner member 360 may be produced with a toothed or untoothed cutting window. In either case, the cross-section of the inner member shown in FIGS. 35 and 36 will be similar.

The sharpened, non-toothed inner member shown in FIGS. 8–11 as inner member 50 could also be combined with outer member 330 to produce a sharper cutting action than that offered by the combination of FIG. 35. If the inner member is additionally provided with teeth that are sharpened to a point at the radially outermost portion of each tooth (adjacent the innermost portion of edges 309 or 339) the sharpness of the cut will be even further enhanced.

Figure 37:
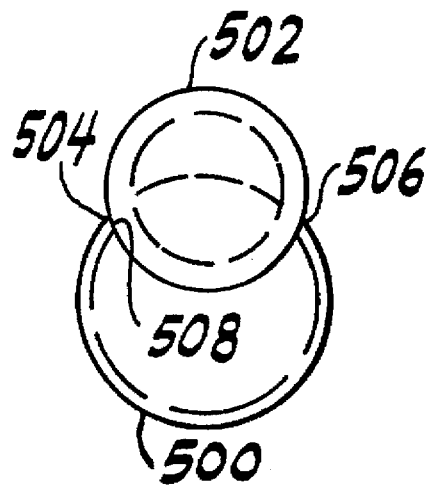
FIG. 37 is a cross-sectional view of an inner tubular member during a process of forming sharpened edges around an opening of the member.
Figure 38:
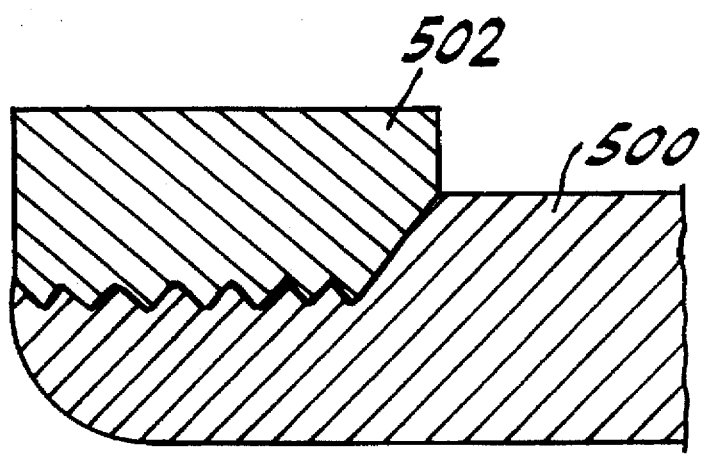
FIG. 38 is a side elevational view of FIG. 37.

One method of forming such a sharpened toothed or non-toothed inner member is shown in FIGS. 37 and 38 in which an electrochemical grinding machine or an electrical discharge machine may be used to produce sharpened edges or teeth in the cutting window of an inner tubular member 500. Tool 502 could be a rotating wheel in the case of electrochemical grinding machine or a non-rotating electrode in the case of an electrical discharge machine. In each case the tool has a diameter smaller than that of the tubular member so the sharpened edge is formed on the radially outermost surface of the member. Moving the tool toward inner member 500 such that the intersection of tool 502 with the outer surface of tubular member 500 would produce opposing sharpened outer edges 504 and 506. The edges could be produced with or without teeth. It will be understood that replacing member 360 of FIG. 36 with inner tubular member 500 will replace flat surface 362 with an angled surface 508 thereby producing a sharper cut.

It will be understood by those skilled in the art that numerous improvements and modifications may be made to the preferred embodiment of the invention disclosed herein without departing from the spirit and scope thereof.

What is claimed is:

1. Method of forming an opening at one end of an elongated tubular surgical shaver blade having a distal end and a proximal end, comprising the steps of:
    providing an apparatus for performing an electrochemical grinding process on a portion of the elongated tubular surgical shaver blade, the apparatus having a rotatable abrasive wheel with a perimetral surface which has a circumferential groove formed therein, said groove having a predetermined arcuate profile in a radial plane of said wheel;
    orienting the distal end of the elongated tubular surgical shaver blade in a predetermined orientation relative to said wheel;
    activating said apparatus to perform an electrochemical grinding process; and
    moving the distal end of the elongated tubular shaver blade relative to said wheel during the performance of said electrochemical grinding process to perform the electrochemical grinding process on the distal end of the elongated tubular surgical shaver blade to thereby form an opening therein.

2. A method according to claim 1 wherein said wheel is planar, wherein said elongated tubular surgical shaver blade has an axis and wherein said step of orienting further comprises securing the tubular shaver blade in a fixed position with its axis aligned within the plane of said wheel and further comprising the step of moving the distal end of the elongated tubular surgical shaver blade tangentially relative to said wheel.

3. A method according to claim 1 wherein said predetermined arcuate profile comprises an arc having a predetermined radius of curvature.

4. A method according to claim 1 wherein said distal end of the elongated tubular surgical shaver blade comprises an end which is initially closed.

5. A method according to claim 1 wherein said step of moving further comprises moving said elongated tubular shaver blade in a linear path relative to a predetermined tangential point on said wheel.

6. A method according to claim 1 wherein said step of moving further comprises moving said elongated tubular shaver blade in a curvilinear path relative to a predetermined tangential point on said wheel.

7. A method according to claim 6 wherein said predetermined orientation is such that said elongated tubular shaver blade is aligned within said radial plane of said wheel.

8. A method of shaping an opening in a predetermined portion of a tubular member of a rotary shaver blade, said predetermined portion having an axis, said method comprising the steps of:
    providing a hollow tubular member having an axis, a distal end and a proximal end;
    providing a grinding wheel having an axis and a predetermined arcuate groove in its perimetral surface, said groove for creating in said tubular member an arcuate surface having at least one predetermined radius of curvature;
    orienting said axis of said predetermined portion of said tubular member at a predetermined angle relative to a line tangent to said wheel;
    rotating said grinding wheel about its axis;
    advancing said predetermined portion of said tubular member along a path which intersects with a selected portion of said grinding wheel whereby such motion will result in an opening being shaped in said predetermined portion of said tubular member.

9. A method according to claim 8 wherein said predetermined portion of said tubular member is the distal tip thereof.

10. A method according to claim 8 wherein said grinding wheel is an electrode component of a electrochemical grinding apparatus.

11. A method according to claim 8 wherein said orienting step further comprises aligning the axis of said tubular member perpendicular to the axis of said wheel.

12. A method according to claim 8 wherein said orienting step further comprising aligning the axis of said tubular member parallel to the axis of said wheel.

13. A method of shaping an opening in a tubular member of a rotary shaver blade comprising the steps of:

providing a cylindrical forming apparatus having a circumferential surface for shaping in said tubular member an opening, said circumferential surface situated at a predetermined radius from a first axis and being movable about said first axis;

fixedly mounting a hollow tubular member with its axis parallel to said first axis;

rotating said axis of said tubular member about a second axis parallel to said first axis, the distance between said first and second axes being greater than said predetermined radius and such that during rotation of said axis of said tubular member about said second axis a predetermined portion of said tubular member will intersect a predetermined portion of said circumferential surface.

14. A method according to claim 13 wherein said tubular member is fixedly mounted with its distal end adjacent said circumferential surface.

15. A method according to claim 13 wherein said tubular member has a closed distal end.

16. A method according to claim 13 wherein said circumferential surface further comprises a predetermined profile having a plurality of circumferential notches adapted to produce a toothed opening in said tubular member.

17. A method according to claim 13 wherein said circumferential surface comprises, relative to said first axis, a radially outermost portion and a radially innermost portion, wherein said circumferential surface rotates about said first axis and said tubular member rotates about said second axis, said second axis being spaced from said radially innermost portion by a distance which is less than the sum of the radius of said tubular member and the distance between said tubular axis and said second axis.

* * * * *